(12) United States Patent  
Raycheck et al.

(10) Patent No.: US 8,187,246 B2
(45) Date of Patent: May 29, 2012

(54) STRUCTURALLY OPTIMIZED COMPONENT

(75) Inventors: Jeromy Thomas Raycheck, Lebanon, OH (US); Oscar Antonio Ruiz, Mason, OH (US); Mark James Kline, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 740 days.

(21) Appl. No.: 11/934,123

(22) Filed: Nov. 2, 2007

(65) Prior Publication Data

US 2008/0114324 A1 May 15, 2008

Related U.S. Application Data

(60) Provisional application No. 60/856,522, filed on Nov. 3, 2006.

(51) Int. Cl.
*A61F 13/15* (2006.01)
(52) U.S. Cl. .................. 604/391; 604/386; 24/593.1
(58) Field of Classification Search .................. 604/386, 604/391–392; 24/593.1
See application file for complete search history.

(56) References Cited

U.S. PATENT DOCUMENTS

| | | | |
|---|---|---|---|
| 3,494,361 A * | 2/1970 | Thivat | ............................ 604/398 |
| 3,860,003 A | 1/1975 | Buell | |
| 4,515,595 A | 5/1985 | Kievit et al. | |
| 4,695,278 A | 9/1987 | Lawson | |
| 4,699,622 A | 10/1987 | Toussant et al. | |
| 4,728,326 A * | 3/1988 | Gilles | ............................ 604/391 |
| 4,909,803 A | 3/1990 | Aziz et al. | |
| 5,151,092 A | 9/1992 | Buell et al. | |
| 5,176,671 A | 1/1993 | Roessler et al. | |
| 5,221,274 A | 6/1993 | Buell et al. | |
| 5,518,801 A | 5/1996 | Chappell et al. | |
| 6,120,487 A | 9/2000 | Ashton | |
| 6,251,097 B1 | 6/2001 | Kline et al. | |
| 6,290,687 B1 * | 9/2001 | Skog et al. | ................... 604/391 |
| 6,432,098 B1 | 8/2002 | Kline et al. | |
| 6,689,116 B1 * | 2/2004 | Ekdahl et al. | ................. 604/391 |
| 6,736,804 B1 | 5/2004 | Robertson et al. | |
| 6,936,039 B2 | 8/2005 | Kline et al. | |
| 2003/0233082 A1 | 12/2003 | Kline et al. | |
| 2004/0055123 A1 | 3/2004 | Jackson et al. | |
| 2007/0078426 A1 | 4/2007 | Kline et al. | |
| 2007/0078427 A1 | 4/2007 | Raycheck et al. | |
| 2007/0093769 A1 | 4/2007 | Kline et al. | |

FOREIGN PATENT DOCUMENTS

| | | |
|---|---|---|
| EP | 0 548 050 A2 | 6/1993 |
| WO | WO 99/11211 A1 | 3/1999 |
| WO | WO 03/010574 A2 | 2/2003 |
| WO | WO 2007/036899 A2 | 4/2007 |
| WO | WO 2007/036908 A2 | 4/2007 |
| WO | WO 2007/036910 A2 | 4/2007 |
| WO | WO 2007/036918 A1 | 4/2007 |

* cited by examiner

*Primary Examiner* — Lynne Anderson
(74) *Attorney, Agent, or Firm* — Laura L. Whitmer; Abbey A. Lopez

(57) ABSTRACT

A structurally optimized component comprising a fastening member having a middle section and an end section, wherein either the middle section comprises an inner slot leg region, an outer slot leg region, and an interior low mass slot leg region or the end section comprises a slot reinforcement having an inner reinforcement region, an outer reinforcement region, and an interior low mass reinforcement region.

15 Claims, 4 Drawing Sheets

STRUCTURALLY OPTIMIZED COMPONENT

CROSS REFERENCE TO RELATED APPLICATION

This application claims the benefit of U.S. Provisional Application No. 60/856,522, filed Nov. 3, 2006, the substance of which is incorporated herein by reference.

FIELD OF THE INVENTION

The present invention relates to absorbent articles, which are capable of absorbing bodily exudates, having structurally optimized components.

BACKGROUND OF THE INVENTION

"Surface fasteners" are commonly used in many applications, such as disposable incontinence articles (diapers), to join a first surface to a second surface, thereby connecting a first and second portion of an article in face-to-face relationship. Surface fasteners include fastening systems such as "hook & loop" (ie, Velcro™), adhesive or cohesive tapes, magnets, etc. While known to form good connections, surface fasteners can be hard to align, especially when used on diapers & the like in which the product being fastened is applied to a wearer who may move. Also, many types of surface fasteners stick to many things they are not supposed to (ie, tapes to skin, hooks to clothing/carpet. etc.) and can be noisy to unfasten.

Other types of fasteners, generically referred to as "macrofasteners", which are large, interlocking fasteners, solve many of the problems associated with surface fasteners. Macrofasteners tend to result in good alignment of parts to be connected, typically only interlock with themselves (and do not stick to other objects), & many are very quiet to disengage. Typical macrofasteners include buckles, tabs & slots, hooks and eyes, buttons, and the like.

A drawback of the macrofastener is the rigidity required to make them function correctly. Rigidity is required to prevent the macrofastener from deforming significantly during the engagement process, causing the two components of the fastener to form shapes that do not readily mate together. In addition, the loads that macrofasteners are required to sustain during use may add additional strength requirements requiring even more rigidity of the components to prevent them from deforming or even fracturing during use.

In the field of disposable absorbent articles such as diapers, adult incontinence products, and feminine hygiene products, macrofasteners can be attached to the article and used to join portions of the article to form waist and leg openings. To ensure that the product fits properly and stays in the right location around the torso of the user, a certain tensile force must pass through the waist and the leg openings. The macrofastener must be strong enough to withstand this force sufficiently so it will not be subject to the deformation or fracture as described above It is common in the field of disposable absorbent articles to use materials such as plastics and polymers to form macrofasteners because of there ability to readily be formed into shapes that are suitable for such applications. The macrofastener may comprise a core component useful in providing strength and a nonwoven cover that provides softness. With polymers, the price of the base material tends to get higher as the materials get stronger and stronger. In addition, it's obvious to those skilled in the art that the more material that is used, the more the components are likely to cost.

There are 2 commonly known ways to make the core fastener elements rigid enough to bear the required loads: 1) use a material that is stronger (ie has a higher modulus of elasticity, or 2) add more of the material to strengthen the components.

Unfortunately, both of these methods of strengthening the core components generally results in a higher cost of manufacture to achieve proper function, and if translated to the consumer, may decrease the economy of the product or result in a poor value to the consumer.

Therefore, to achieve a good value to the consumer, there is a need to have a macrofastener or other force transferring element that has a maximum strength while using 1) a minimum elastic modulus, and 2) a minimum amount of material.

SUMMARY OF THE INVENTION

The present invention is directed to a structurally optimized component comprising a fastening member having a middle section and an end section, wherein either the middle section comprises an inner slot leg region, an outer slot leg region, and an interior low mass slot leg region or the end section comprises a slot reinforcement having an inner reinforcement region, an outer reinforcement region, and an interior low mass reinforcement region.

BRIEF DESCRIPTION OF THE DRAWINGS

In the accompanying drawing, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

DETAILED DESCRIPTION OF THE INVENTION

Figure 1A:
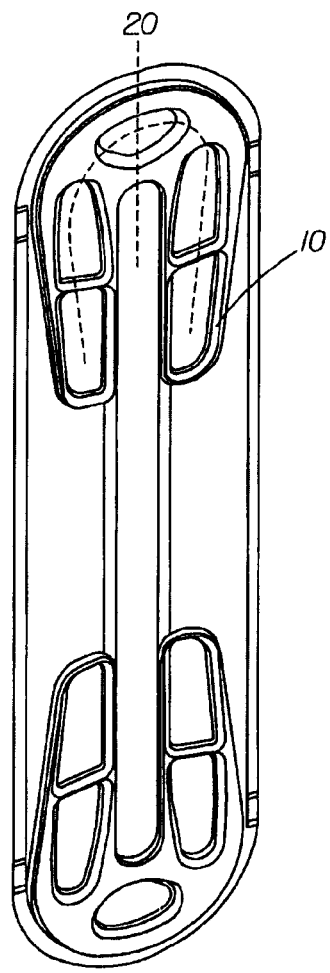
FIGS. 1a-d illustrate a bending modulus example in accordance with the present invention.
Figure 1B:
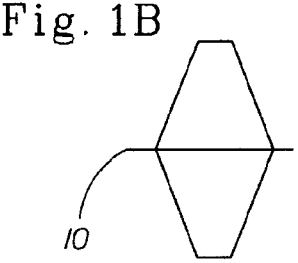

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like. Absorbent articles may be disposable or may have portions that may be restored or renewed.

The present invention is directed to a structurally optimized component design that can provide maximum rigidity using a minimum amount of material and a minimum modulus of elasticity. Given an initial component design, by structurally reinforcing the higher stress or higher deflection areas of the components (when under load) and removing materials in the lower stress or lower deformation regions, the component can be designed to limit the deflection of the component under that loading condition.

Generally, the most efficient way to achieve an optimized component design is through the use of Finite Element Analysis Techniques with the aid of software that is designed to help with such calculations. Through a process of genetic iteration, it is possible to achieve more and more optimized designs until the design is optimized to within practical limits. In certain cases, there is software that is designed to aid the evolution process, as well. Another, less efficient but still plausible way to optimize is through the use of destructive testing and trial and error methodology. Thus, the present invention is directed to a structurally optimized component design. Designs of the present invention use less material while achieving the same deflection performance versus other, less optimized designs using more mass.

In addition to leg and waist forces, it may be important to transfer other forces acting on the article to other areas of the article to be able to achieve the best fit possible. Doing this may require the use of rigid force transferring elements within the article as the nature of the forces could not only be in tension, but compression and torsion, too. An example of this would be to transfer some of the force around the leg opening up to the top of the waist opening of the article to hold the waist as high as possible. Another embodiment includes the addition of stiffening elements into the diaper that could aid in pull-on and removal of the product. The present invention relates to stiffening elements that are optimized for strength using as little material as possible.

Another advantage of the structurally optimized component designs are the ability to be processed more easily due to: 1) reduced part mass, and 2) increased surface area. These two characteristics offer several distinct advantages during the thermoforming process.

Reduced part mass means that there will be less flow of material per part and therefore, you may be able to use pumps or extruders with reduced size that are less expensive. In addition, the lower the part mass, the easier and faster the part can cool and solidify in certain thermoforming processes. The increased surface area of the component means that there is more area exposed to the ambient conditions or to any cooling mechanism that is used in the process. The rate of cooling is directly related to the amount of surface area exposed to the lower temperature.

Any solid material can be used in this fashion to form components that use less material mass. In general, in the field of disposable absorbent articles, thermoformed plastics are the primary material used. The thermoplastic material may be made of any material capable of yielding the desired properties and can bear loads that are typically seen in particular fastener embodiments. These materials generally include plastics (PE, PP, PET, PA, etc.), and plastics with fillers to increase the elastic modulus (fillers can be wood, wood flour, carbon fiber, calcium carbonate, etc.) but could also include other materials that can be formed with extrusion processes like Metals, ceramics, composites, or co-extruded materials.

Thus, the present invention is directed to a structurally optimized component comprising a fastening member having a middle section and an end section, wherein either the middle section comprises an inner slot leg region, an outer slot leg region, and an interior low mass slot leg region or the end section comprises a slot reinforcement having an inner reinforcement region, an outer reinforcement region, and an interior low mass reinforcement region.

The present invention is further directed to absorbent articles having a front waist region, a back waist region opposed to the front waist region, and a crotch region located between the front waist region and the back waist region, a pair of longitudinal edges and a pair of end edges, the absorbent article comprising: a topsheet; a backsheet; and a fastening system for joining at least a portion of the first waist region with at least a portion of the second waist region, the fastening system including a structurally optimized component comprising a slot member having a middle section and an end section, wherein either the middle section comprises an inner slot leg region, an outer slot leg region, and an interior low mass slot leg region or the end section comprises a slot reinforcement having an inner reinforcement region, an outer reinforcement region, and an interior low mass reinforcement region.

One aspect of the present invention, specifically relating to a fastening mechanism, is directed to structurally optimized component designs comprising a slot reinforcement that is designed to achieve a better ratio of gapping resistance to part mass versus other slot reinforcements. By examining the primary direction of bending when subjected to very small loads, a plane can be created through a component that runs perpendicular to that direction. This direction can be described as the cross section of bending (20), as shown in FIG. 1, assuming the component is isotropic/homogeneous. Considering the cross section, it is possible to calculate the centroid of this cross sectional area. The centroid can be described as the average of the differential areas of the cross section, or the point that represents center of area. The following differential equations may be used to calculate the centroid:

$$Cx=\int xdA/A;\ Cy=\int ydA/A$$

wherein Cx, Cy is the distance from one end of a cross section to the centroid; x, y is the distance from that end of the cross section to the differential area; dA is the differential area; A is the total area.

For this particular cross section of bending, a plane can be defined that passes through the centroid and is perpendicular to the cross section of bending. This plane is the neutral axis. Thus, the present invention is directed to a slot reinforcement having more material disposed away from the neutral axis of bending that disposed toward it on either side of the neutral axis of bending. This ensures a more optimal material usage versus other configurations. There exists an infinite number of cross sections of bending (20) throughout each component. A centroid can be calculated for each, as described above. A neutral axis, for a component, can be determined by creating a plane that is perpendicular to each cross section of bending and passes through each centroid.

Figure 1C:
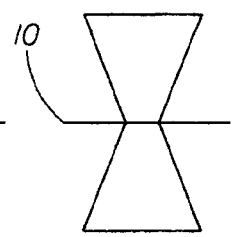
Figure 1D:
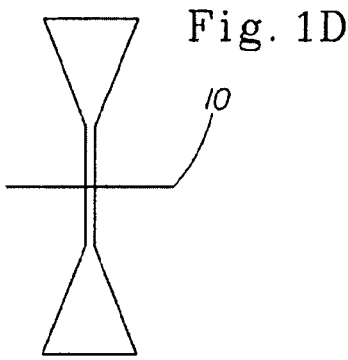

An exemplary neutral axis (10) of the present invention is shown in FIG. 1a. For instance, in viewing the cross sections of bending shown in FIGS. 1b, c, and d all have approximately equal cross sectional areas, and assuming they are of the same material and homogeneous/isotropic, they resist bending to different degrees. FIG. 1c would resist bending significantly more than FIG. 1b; FIG. 1d would resist bending significantly more than FIG. 1c. This is because portions further away from the neutral axis (10) of FIG. 1d (and to some extent FIG. 1c as compared to FIG. 1b) have more cross sectional area than those adjacent to the neutral axis (10), as in FIG. 1b.

Another factor to consider in the present invention is that the material on either side of the neutral axis should be connected by a sufficiently ridged member or members that will prevent slippage of the area above the neutral axis past the area below the neutral axis when subjected to bending. This connector can be a film, a web, a beam, or a series of beams, but it should have a sufficient torsional or shear resistance that can prevent slippage.

Figure 2:
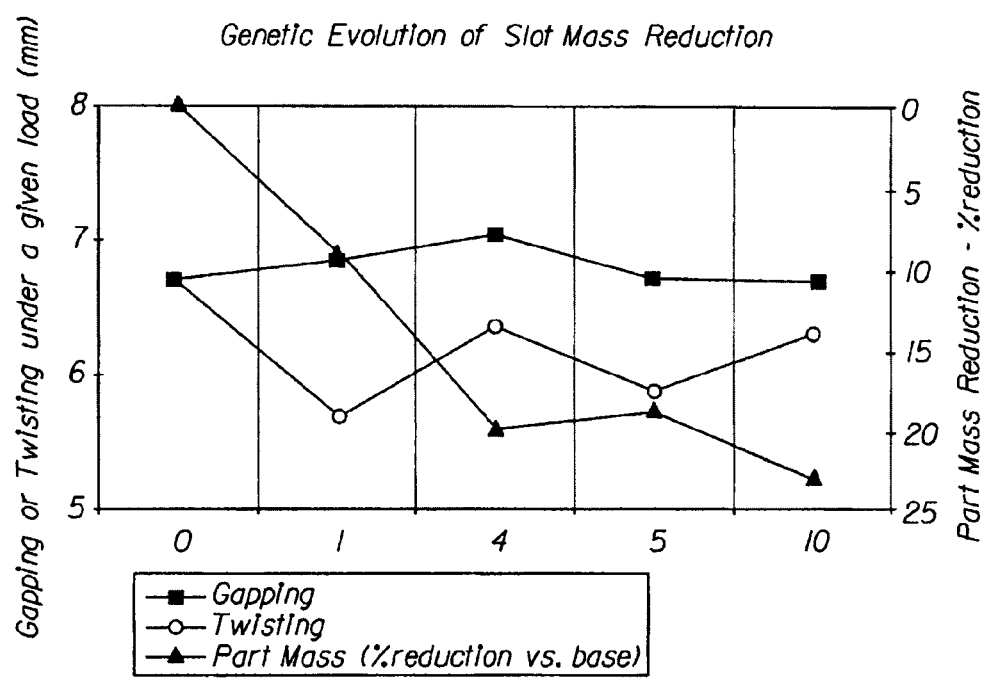
FIG. 2 illustrates information obtained in accordance with one embodiment of the present invention.

A slot reinforcement design that has both more material disposed away from the neutral axis of bending than disposed toward it on either side of the neutral axis of bending and a connector of sufficient strength will be stronger than others of similar mass without this arrangement. Therefore, it is possible to use this arrangement on components that have less mass while achieving similar strength to those having more mass. FIG. 2, shows the structurally optimized component of the present invention. The figure demonstrates an example of an end section slot reinforcement that has been optimized through a series of genetic iterations to within a practical limit for gapping and twisting resistance.

Figure 3:
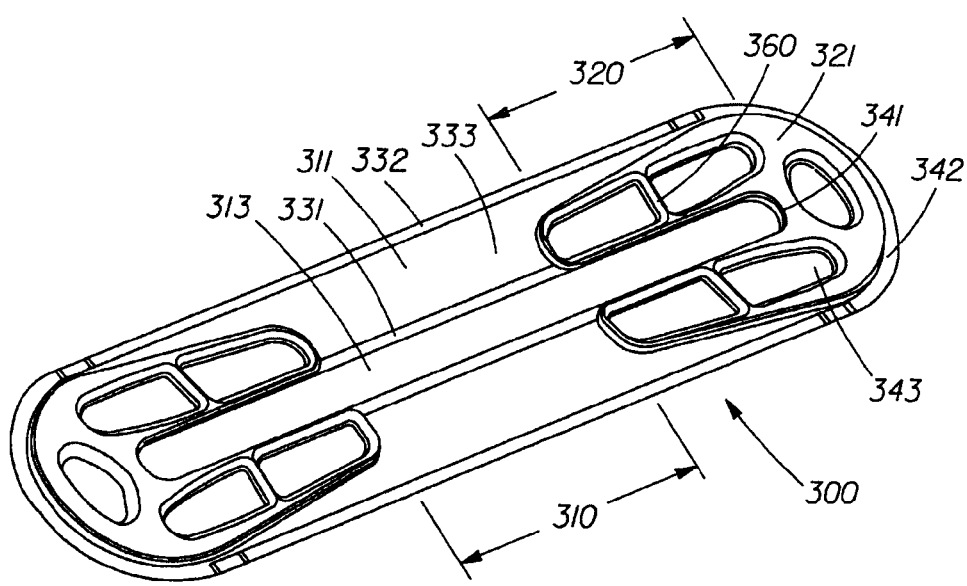
FIG. 3 illustrates an embodiment of the structurally optimized component of the present invention.

A slot member (300), as shown in FIG. 3 has a middle section (310) and an end section (320). This middle section has a pair of slot legs (311) and a slot opening (313). Each slot leg has an inner slot leg region (331), an outer slot leg region (332), and an interior section which defines an interior low mass slot leg region (333). The interior low mass slot leg region has a lower thickness, lower basis weight, lower density, higher ratio of void to non-void space, or higher elastic modulus versus the inner slot leg region or the outer slot leg region. The thickness, basis weight, density, ratio of void to non-void space, or elastic modulus may be the same or different between the inner slot leg region and the outer slot leg region.

In one embodiment, the thickness, basis weight, density, ratio of void to non-void space, or elastic modulus of the interior low mass slot leg regions may be lower by about 50% versus the inner slot leg regions and/or the outer slot leg regions. Alternatively, the thickness, basis weight, density, ratio of void to non-void space, or elastic modulus may be lowered anywhere from about 10% to about 100% of the corresponding measurement of the inner slot leg regions and/or outer slot leg regions. In order to measure the component, samples should be equilibrated in a conditioned room maintained at about 23±2° C. and about 50±2% relative humidity for at least two hours before testing. Any measurements should be taken with no external load (other than gravity) applied to the sample. Thickness measurements should be taken in a manner that exerts less than or equal to ~1 PSI applied to the sample.

Alternatively, the inner slot leg regions and the outer slot leg regions may have at least one structural connector between them. The connector(s) can be of the same thickness as the inner and outer slot leg regions, or the connector may be from about 5% to about 100% of their thickness. Alternatively, the connectors may be from about 100% to about 300% of the thickness of the inner and outer slot leg region. The connectors can be arranged at various angles, i.e. perpendicular to the inner and outer region, or at any angle. The connector should join at least some portion(s) of the inner slot leg region to some portion(s) of the outer slot leg region to leverage the optimization design principle. The thickness of the outer region can be from about 0.25 mm to about 1.0 mm or greater.

The slot member, as shown in FIG. 3, also comprises an end section (320), which comprises a slot reinforcement (321). In the present invention, the slot end section is a mass and strength optimized end reinforcement. The slot reinforcement has an inner reinforcement region (341), an outer reinforcement region (342), and an interior section which defines an interior low mass reinforcement region (343). The interior low mass reinforcement region has a lower thickness, lower basis weight, lower density, higher ratio of void to non-void space, or lower elastic modulus vs. the outer regions. In one embodiment, the thickness, basis weight, density, ratio of void to non-void space, or elastic modulus of the interior low mass reinforcement regions may be lower by about 50% versus the inner reinforcement regions and/or the outer reinforcement regions. Alternatively, the thickness, basis weight, density, ratio of void to non-void space, or elastic modulus may be lowered anywhere from about 10% to about 100% of the corresponding measurement of the inner reinforcement regions and/or outer reinforcement regions. This could mean that a different, potentially lower cost material could be used in the middle section. In another case, the ratio of void space to non-void space within the interior region could be a ratio of from about 20 to about 1; from about 1 to about 1; or from about 1 to about 20.

Within the interior low mass region of the slot reinforcement, it may be desired in some applications to provide a structural connector (360) between the inner and outer regions to prevent them from slipping past each other during bending. The connectors can be made in various forms. It some loading conditions, it is important to have at least one structural connector. In another case, it may be important to have multiple connectors. The connectors may be at various angles between the inner and outer regions, but preferably, the connector connects at least some portion of the inner and outer reinforcement regions. These connectors can be created in multiple other ways, but it is common that they be of comparable strength to the inner and outer reinforcement regions in order to maintain the strength of the system.

In one embodiment, in the slot reinforcement, the primary connection between the inner and outer reinforcement regions is provided through a series of beams that interconnect the three regions simultaneously (the inner reinforcement region, the outer reinforcement region, and the reduced thickness area of the interior low mass region). This results in a particularly strong reinforcement that can resist deformation in multiple directions at once.

In one embodiment, the perimeter of the slot member is wider than the perimeter of the slot reinforcement. The reason for this is so that there is some material outside of the perimeter of the slot reinforcement that is more flexible than the slot reinforcement that can provide a cushioning effect when in close contact to the wearer. In other cases, the perimeter of the reinforced section can coincide with the perimeter of the slot member, or be integral to the slot member. In other cases, the perimeter of the slot reinforcement may be wider than the slot member, as this may be a way to provide additional material that is disposed further away from the neutral axis of bending. Alternatively, the entire slot reinforcement can be integral to the slot member.

Figure 4:
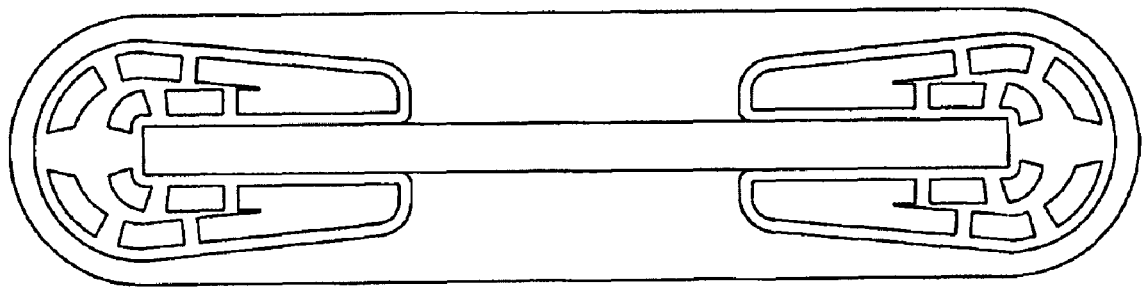
FIG. 4 illustrates an embodiment of the structurally optimized component of the present invention.

The slot reinforcement may be located at various portions of the slot member. In yet another embodiment, as shown in FIG. 4, the end section of the slot member may comprise a slot reinforcement having reinforcement in the center of the member. For certain geometries, it may be necessary to use a reinforcement disposed between the inner and outer regions to aid in the connection of the inner reinforcement region to the outer reinforcement region. The reinforcement slot has an inner reinforcement region, an outer reinforcement region, and an interior section which defines an interior low mass region. Within the low mass region, the slot reinforcement has a supplemental support that is disposed in between the inner and outer regions. Within the interior region, the slot reinforcement has a series of connector beams that interconnect the exterior reinforcement region to the supplemental reinforcement, and further connect the supplemental reinforcement to the interior reinforcement region. The interior low mass region has a thickness, basis weight, density, increased ratio of void to non-void space, or elastic modulus versus the outer regions.

The present invention may also be used as the tab portion of a fastening component. Tab and slot configurations are described in the following publications: WO 2007/036918; WO 2007/036910; WO 2007/036908; WO 2007/036899; WO 2003/10574; WO 1999/011211. While these publications describe how tab/slot fastening systems are incorporated into absorbent articles, none describe the optimized component of the present invention. The component of the present invention is useful in the various type of absorbent articles described herein.

In other examples, the component may not be a slot, but may a member designed to bear a torsional or compressive load to carry a force from one area of an article to another while using the same mass optimization principles that were described above. There may still be an inner reinforcement region, an outer reinforcement region, and interior low mass region that are designed to achieve the same objective, to achieve the maximum strength for minimum materials usage. In these cases, the loads may be analyzed and the components may be designed accordingly to optimize material usage for the loading conditions that are at play. In some cases, it may be advantageous that the component be optimized for bending in multiple directions, which may result in shapes that are far less planar than the slots that were shown.

It is not necessary for the component of the present invention to have both an interior low mass slot leg region and an interior low mass reinforcement region. The component may have only one of the interior low mass regions or both.

In one embodiment, the load bearing element is roughly "+" shaped cross section, with each leg of the "+" being shaped like a "T" with the base of the "T" at the center of the "+" and the top of the T at the outboard edges. In some examples, the shape may be identical in the X and Y directions. In another example, the shape may be wider in the x-direction and narrower on the y-direction or vice versa. In this example, the shape results in four exterior beams that define the exterior reinforcement region, an interior region with a "+" shaped cross section that defines an interior low mass region. The interior region serves as the structural connection between the four exterior reinforcement regions. The interior region has a lower thickness, lower basis weight, lower density, higher ratio of void to non-void space, or lower elastic modulus versus the outer regions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A structurally optimized component comprising a fastening member having a middle section and an end section, wherein said middle section comprises a pair of slot legs and a slot opening, wherein each slot leg has an inner slot leg region located adjacent the slot opening, an outer slot leg region, and an interior low mass slot leg region disposed between the inner slot leg region and the outer slot leg region; wherein said end section comprises a slot reinforcement having an inner reinforcement region located adjacent the slot opening, an outer reinforcement region, and an interior low mass reinforcement region disposed between the inner reinforcement region and the outer reinforcement region.

2. The component of claim 1, wherein said slot reinforcement has more material disposed away from a neutral axis of bending than disposed toward said neutral axis of bending.

3. The component of claim 1, wherein said middle section comprises a connector to connect material on either side of a neutral axis of bending.

4. The component of claim 3, wherein said connector has a thickness of from about 5% to about 100% relative to the thickness of said inner slot leg region and said outer slot leg region.

5. The component of claim 3, wherein said connector has a thickness of from about 100% to about 300% relative to the thickness of said inner slot leg region and said outer slot leg region.

6. The component of claim 1, wherein said slot reinforcement comprises a connector to connect material on either side of a neutral axis of bending.

7. The component of claim 6, wherein said connector has a thickness of from about 5% to about 100% relative to the thickness of said inner reinforcement region and said outer reinforcement region.

8. The component of claim 6, wherein said connector has a thickness of from about 100% to about 300% relative to the thickness of said inner reinforcement region and said outer reinforcement region.

9. The component of claim 1, wherein said interior low mass slot leg region has a lower thickness, lower basis weight, and lower density relative to said inner slot leg region and said outer slot leg region.

10. The component of claim 1, wherein said interior low mass reinforcement region has a lower thickness, lower basis weight, and lower density relative to said inner reinforcement region and said outer reinforcement region.

11. The component of claim 1, wherein said interior low mass slot leg region is reduced from about 10% to about 100% as compared to said inner slot leg region and said outer slot leg region.

12. The component of claim 1, wherein said interior low mass reinforcement region is reduced from about 10% to about 100% as compared to said inner reinforcement region and said outer reinforcement region.

13. The component of claim 1, wherein said component is made of a thermoplastic material.

14. An absorbent article having a front waist region, a back waist region opposed to the front waist region and a crotch region located between the front waist region and the back waist region, a pair of longitudinal edges and a pair of end edges, the absorbent article comprising:
   a topsheet;
   a backsheet; and
   a fastening system for joining at least a portion of said front waist region with at least a portion of said back waist region, the fastening system comprising a structurally optimized component comprising a fastening member having a middle section and an end section, wherein said middle section comprises a pair of slot legs and a slot opening, wherein each slot leg has an inner slot leg region located adjacent the slot opening, an outer slot leg region, and an interior low mass slot leg region disposed between the inner slot leg region and the outer slot leg region; wherein said end section comprises a slot reinforcement having an inner reinforcement region located adjacent the slot opening, an outer reinforcement region, and an interior low mass reinforcement region disposed between the inner reinforcement region and the outer reinforcement region.

15. A structurally optimized component comprising a fastening member having a middle section and an end section, wherein said middle section comprises a pair of slot legs and a slot opening, wherein said end section comprises a slot reinforcement having an inner reinforcement region located adjacent the slot opening, an outer reinforcement region, and an interior low mass reinforcement region disposed between the inner reinforcement region and the outer reinforcement region.

* * * * *